United States Patent
Tatum, III

[11] Patent Number: 5,092,771
[45] Date of Patent: Mar. 3, 1992

[54] ROTARY DENTAL IMPLANT POST

[76] Inventor: O. Hilt Tatum, III, 2299 - 9th Ave. N., Ste 1E, St. Petersburg, Fla. 33713

[21] Appl. No.: 616,340

[22] Filed: Nov. 21, 1990

[51] Int. Cl.⁵ .............................................. A61C 8/00
[52] U.S. Cl. .................................................... 433/173
[58] Field of Search ................. 433/173, 174, 175, 176

[56] References Cited

U.S. PATENT DOCUMENTS

| | | |
|---|---|---|
| 2,835,033 | 5/1958 | Airosser . |
| 3,474,537 | 10/1969 | Christensen . |
| 3,497,953 | 3/1970 | Weissman . |
| 3,672,058 | 6/1972 | Nikoghossian . |
| 3,683,501 | 8/1972 | Edelman . |
| 3,738,004 | 6/1973 | Edelman . |
| 3,777,402 | 12/1973 | Roberts . |
| 3,798,771 | 3/1974 | Edelman . |
| 3,849,887 | 11/1974 | Brainin . |
| 3,849,888 | 11/1974 | Linkow . |
| 3,908,269 | 9/1975 | Christenot et al. . |
| 3,950,850 | 4/1976 | Driskell et al. . |
| 4,060,896 | 12/1977 | Wahnish . |
| 4,177,562 | 12/1979 | Miller et al. . |
| 4,217,100 | 8/1980 | Edelman ............................. 433/176 |
| 4,234,309 | 11/1980 | Sellers ................................. 433/225 |
| 4,293,302 | 10/1981 | Hassler ................................ 433/173 |
| 4,302,188 | 11/1981 | Driskell .............................. 433/173 |
| 4,377,382 | 3/1983 | Roberts ............................... 433/176 |
| 4,416,629 | 11/1983 | Mozsary ............................. 433/174 |
| 4,511,335 | 4/1985 | Tatum, Jr. .......................... 433/173 |
| 4,636,216 | 1/1987 | Tatum ................................... 623/16 |
| 4,657,510 | 4/1987 | Gittleman .......................... 433/173 |
| 4,738,623 | 4/1988 | Driskell .............................. 433/173 |
| 4,780,080 | 10/1988 | Haris ................................... 433/174 |

FOREIGN PATENT DOCUMENTS

| | | |
|---|---|---|
| 0198306 | 10/1986 | European Pat. Off. . |
| 2413883 | 3/1974 | Fed. Rep. of Germany . |
| 2600639 | 1/1976 | Fed. Rep. of Germany . |
| 2300540 | 9/1976 | France . |
| 2468352 | 5/1981 | France . |
| 7620101 | 5/1981 | France . |
| 1305478 | 1/1973 | United Kingdom . |

Primary Examiner—Cary E. O'Connor
Attorney, Agent, or Firm—Frijouf, Rust & Pyle

[57] ABSTRACT

An apparatus and method is disclosed for an improved rotary dental implant post for supporting as prosthesis in a patient, comprising as boss having a boss hole defining a boss hole recess. A prosthesis support is secured to a stud with the stud having a stud projection. An undercut is defined in the boss enabling the stud projection to be moved along the bore hole recess and to enter the undercut for enabling free rotation of the support relative to the boss. In one enbodiment of the invention, the stud projection comprises threads disposed on the stud for mating engaging with threads defined in the boss hole. In another embodiment of the invention, the stud projection comprises a key expending from the stud for mating engaging with a keyway defined in the boss hole.

31 Claims, 6 Drawing Sheets

ROTARY DENTAL IMPLANT POST

BACKGROUND OF THE INVENTION

1. Field Of The Invention

This invention relates to a dental implant for securing a prosthesis to a jawbone of a patient, and more particularly to an improved rotary dental implant post for enabling rotation of a support for a prosthesis prior to the final mounting of the prosthesis.

2. Information Disclosure Statement

Presently there exist many types of dental implants designed to enable a prosthesis such as a crown replacement to be rigidly secured tot he jawbone. Probably the most common type of dental implant consists of a threaded pin which is dimension ed to threadably engage the socket of a recently extracted tooth.

U.S. Pat. Nos. 3,589,011 and 4,234,309 and German No. 2,255,916 are illustrative examples of such threaded-type implants. The primary disadvantage to the threaded dental implants is the tendency to loosen within the socket. The dental implant then has to be removed and replaced by a larger diameter implant. For obvious reasons, these threaded type dental implants have not become widely accepted in the art.

U.S. Pat. No. 3,835,033 discloses another type of dental implant which is designed to be inserted within the socket or alveolar cavity of a recently extracted tooth. This dental implant comprises two rods which are inserted into the socket and a plurality of fins and spacers are alternatively slipped onto the rods extending from the socket to achieve the desired height of the dental implant.

U.S. Pat. No. 4,060,896 discloses a threaded-type dental implant wherein a hardenable material is disposed in the jawbone socket prior to the dental implant being threaded therein. The filler material is an attempt to inhibit the dental implant from loosening within the socket of the extracted tooth.

U.S. Pat. No. 3,672,058 illustrates threaded-type dental implant which comprises a self-tapping conical screw. The tape of the self-tapping screw is designed to threadably engage the socket of the extracted tooth and then threadably engage the portion of the jawbone located immediately below the socket.

U.S. Pat. No. 3,474,537 discloses a dental implant comprising a flat configuration with one or more holes extending obliquely therethrough. A threaded fastener is inserted through the oblique holes to threadably engage the lower portion of the lower jawbone thereby preventing rotation of the dental implant.

U.S. Pat. No. 4,531,915 discloses an improved dental implant wherein an implant anchor is implanted into a jawbone of a patient and a prosthesis support is subsequently secured to the implant anchor. This invention discloses a novel means for rotationally orientating the prosthesis support relative to the implant anchor.

It is a primary object of this invention to improve upon the advancement set forth in U.S. Pat. No. 4,531,915 by providing an improved means for rotationally orientating the prosthesis support relative to the implant anchor.

Another object of this invention is to provide a dental implant post which is rigidly secured to a dental implant and which provides a suitable rotational foundation for a prosthesis such as a crown.

Another object ot shis invention is to implant anchor through the implant post which provides a rotational orientation of a prosthesis support relative to the implant anchor through the use of simple, strong and efficient threaded fasteners.

Another object of this invention is to provide a dental implant post wherein stud threads cooperate with the bos threads and an undercut to provide a rotational orientation of a prosthesis support relative to the implant anchor.

Another object of this invention is to provide a dental implant post wherein a key cooperates with a keyway and an undercut to provide a rotational orientation of a prosthesis support relative to the implant anchor.

The foregoing has outlined some of the more pertinent objects of the present invention. These objects should be construed as being merely illustrative of some of the more prominent features and applications of the invention. Many other beneficial results can be obtained by applying the disclosed invention in a different manner or modifying the invention within the scope of the invention. Accordingly other objects in a full understanding of the invention may be had by referring to the summary of the invention, the detailed description describing the preferred embodiment in addition to the scope of the invention defined by the claims taken in conjunction with the accompanying drawings.

SUMMARY OF THE INVENTION

The present invention is defined by the appended claims with specific embodiments being shown in the attached drawings. For the purpose of summarizing the invention, the invention relates to an improved dental implant post for supporting a prosthesis in a patient. The dental implant post comprises a boss having a boss hole defining a boss hole recess. An implant anchor is provides for securing the boss relative to the patient. A support for supporting the prosthesis is secured to a stud having stud projection means. An undercut is defined in the boss for enabling the stud projection means to be moved along the bore hole recess and to enter the undercut for enabling free rotation of the support relative to the boss.

In one embodiment of the invention, the boss hole recess includes boss threads defined in the boss hole and the stud projection means comprises stud threads secured relative to the support for mating engaging with the boss threads. In another of he invention, the boss hole recess includes boss keyway defined in the boss hole and the stud projection means comprises a key extending outwardly from the support for mating engaging with the keyway.

In a more specific embodiment of the invention, the dental implant post comprises a boss having a threaded hole defining boss threads. An implant anchor of varied design secures the boss in the patient. A support is provided for supporting the prosthesis with a stud having stud threads being angularly secured relative to the support. An undercut is defined in the boss enabling the stud threads to be threaded into the boss threads and to enter the undercut for enabling free rotation of the support relative to the boss.

In one embodiment of the invention, a counterbore is defined in the boss and disposed concentrically with the threaded hole. The stud has a shank portion for providing a rotational fit with the counterbore defined in the boss when the stud threads are disposed within the undercut. Preferably, the counterbore has a diameter which is greater than a diameter of the threaded hole for defining a boss shoulder at a junction of the counterbore and the threaded hole. The stud includes a shank portion, an intermediate portion and a threaded portion with the shank portion having a diameter which is greater than a diameter of the intermediate portion for defining a stud shoulder at a junction of the shank portion and the intermediate portion. The shank portion provides a rotational fit with the counterbore when the stud threads are disposed within the undercut.

In still another embodiment of the invention, the undercut is defined in the boss at an inner end of the threaded hole with the stud threads being disposed only at a distal end of the stud. Means are provided for inhibiting rotation of the support relative to the boss. Preferably, the support is cemented to the boss for inhibiting rotation of the support relative to the boss.

The foregoing has outlined rather broadly the more pertinent and important features of the present invention in order that the detailed description that follows may be better understood so that the present contribution to the art can be more fully appreciated. Additional features of the invention will be described hereinafter which form the subject of the claims of the invention. It should be appreciated by those skilled in the art that the conception and the specific embodiments disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims.

BRIEF DESCRIPTION OF THE DRAWINGS

For a fuller understanding of the nature and objects of the invention, reference should made to the following detailed description taken in connection with the accompanying drawings in which.

Similar reference characters refer to similar parts throughout the several Figures of the drawings.

DETAILED DISCUSSION

FIGS. 1-4 illustrate a prior art dental implant 10 as disclosed in U.S. Pat. No. 4,531,915 issued to O. Hilt Tatum Sr. D.D.S. for supporting a prosthesis, such as a crown 11 shown in FIG. 4. The dental implant 10 comprises a central rod 12 having a plurality of fins 14 extending radially from the rod 12. A boss 16 is formed at a proximal end 18 of the rod 12.

The plurality of fins 14 progressively decrease from the proximal end 18 of rod 12 to a distal end 19 of the rod 12 to form a taper to correspond to a taper of a socket of an extracted tooth (not shown). Indentations 20A and 20B are formed on opposing sides of each of the plurality of fins 14 to inhibit rotation of the dental implant 10 after the dental implant 10 is inserted in the socket of the extracted tooth.

Figure 3:
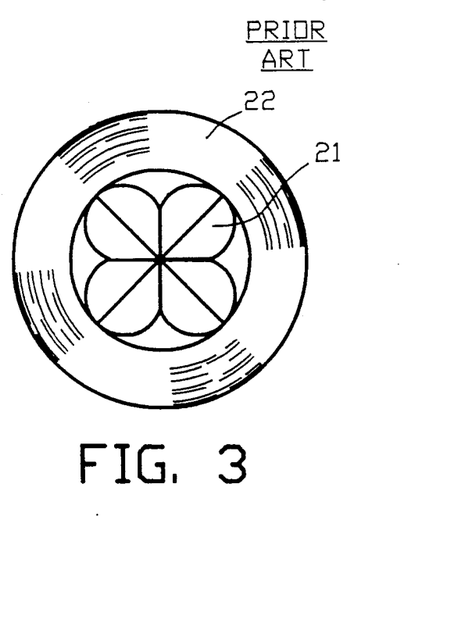
FIG. 3 is a top view of the first prior art dental implant of FIG. 1.
Figure 4:
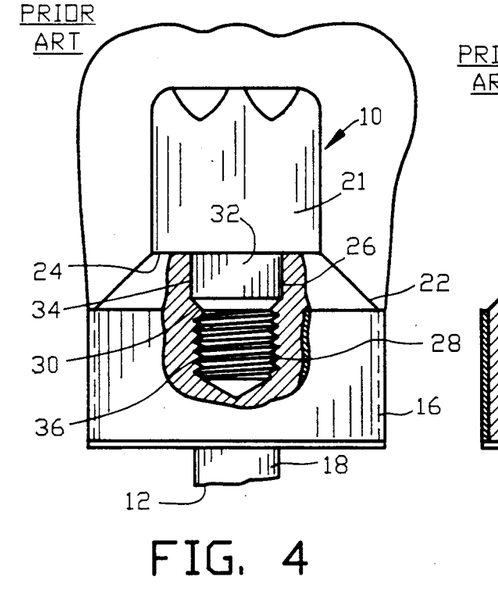
FIG. 4 is an enlarged view of a portion of the first prior art dental implant of FIG. 1 with a crown located on the support.

The boss 16 threadably receives a support 21 to form a base for the prosthesis 11 as shown in FIG. 3. An upper corner 22 of boss 16 is chamfered establishing the diameter of an upper surface 24 of boss 16 to be equal to a diameter of the support 21.

Figure 1:
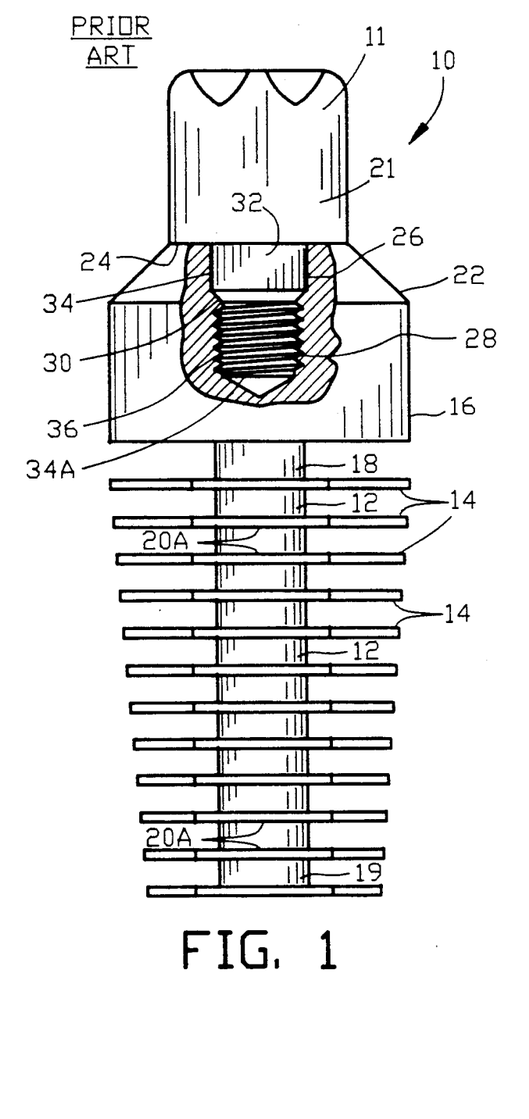
FIG. 1 is a side view partially in section of a first prior art dental implant.
Figure 2:
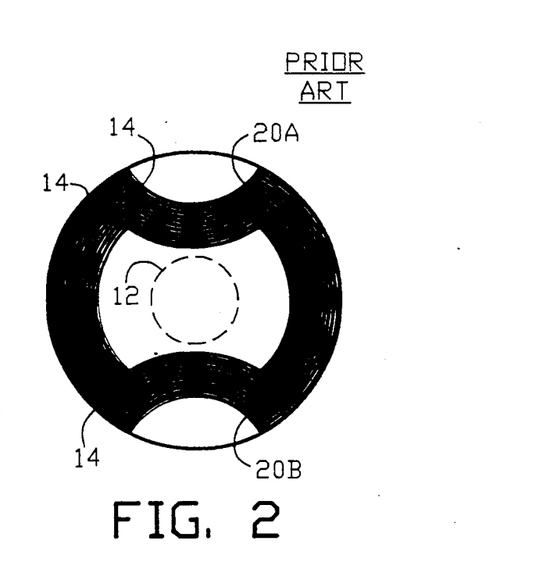
FIG. 2 is a bottom view of the first prior art dental implant of FIG. 1.

A counterbore 26 is axially disposed within the upper surface 24 of boss 16 with a threaded hole 28 extending concentrically from the bottom of the counterbore 26 into the boss 16. The diameter of counterbore 26 is greater than the diameter of the threaded hole 28 to provide a chamfered seat 30 at the junction of the counterbore 26 and the threaded hole 28.

A stud 32 having a shank portion 34 and a threaded portion 36 extends axially from a bottom of the support 21. The length of the shank portion 34 is equal to the depth of the counterbore 26 enabling an end 34A of the shank portion 34 to seat against the chamfered seat 30 of the boss 16 when the support 21 is threaded into the threaded hole 28 as shown in FIG. 1.

The dental implant 10 of FIGS. 1-4 is designed for insertion within a socket (not shown) of a recently extracted tooth or for insertion into an artificially created socket having a configuration similar to the dental implant 10. A conventional cap screw (not shown) is threaded into the threaded hole 28 of boss 16.

After the dental implant 10 is inserted into the socket, the dental implant 10 remains in place for a period of time of approximately four to six months during which the surrounding bony structure will grow between the plurality of fins 14 to rigidly secure the dental implant 10 within the socket. The conventional cap sore threaded into the threaded hole 28 of the boss 16 prevents matter from entering into and contaminating the counterbore 26 in the threaded hole 28 during the healing period. When the dental implant 10 is rigidly secured in the socket, the cap screw is removed and the support 21 is threaded into the boss 16. The prosthesis 11 is then rigidly secured to the support 21 by an adhesive or the like.

Figure 5:
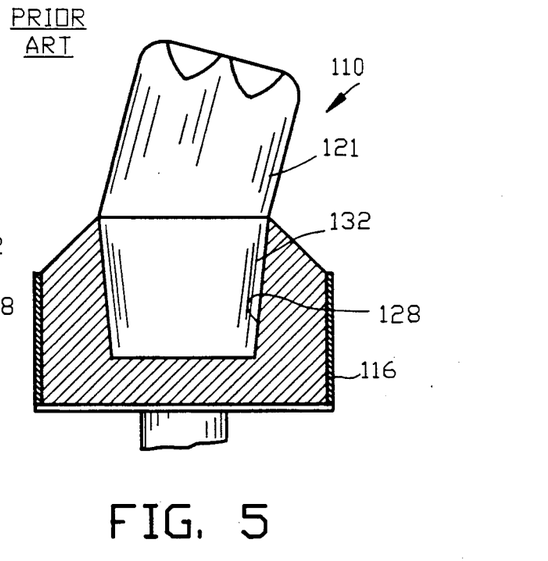
FIG. 5 is a side view partially in section of a second prior art dental implant.

FIG. 5 is a side view partially in section of a second prior art dental implant 110 as disclosed in U.S. Pat. No. 4,531,915 wherein the support 121 is positioned at an angle with respect to the axis of the boss 116. When the support 121 is positioned at an angle with respect to the axis of the boss 116, the support 121 must be rotatable relative to the boss 116 after the dental implant 110 is rigidly secured in the socket to allow proper positioning of the prosthesis 11. To accomplish this rotation, the prior art dental implant 110 incorporated a boss 116 having a tapered socket 128 for receiving a tapered plug 132 extending from the support 121. The tapered plug 132 is of a conical configuration to form a taper lock fit with the socket 128. Accordingly, the tapered plug 132 of the support 121 can be secured at any rotational position relative to the boss 116. After the tapered plug 132 of the support 121 is secured in the proper rotational position relative to the boss 116, the tapered plug 132 is cemented within the tapered socket 128 of the boss 116.

Figure 6:
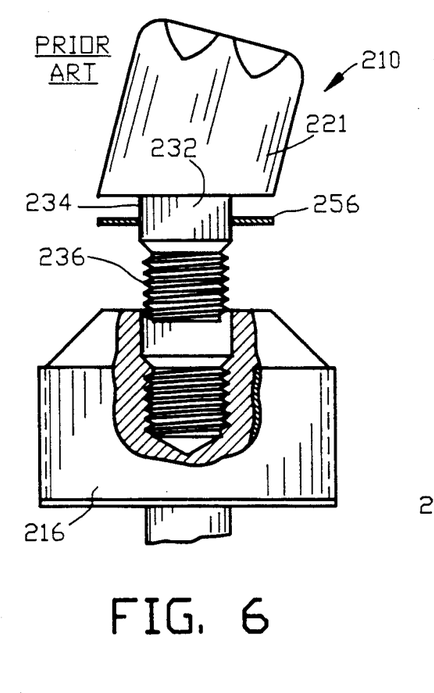
FIG. 6 is an exploded side view partially in section of a third prior art dental implant.
Figure 7:
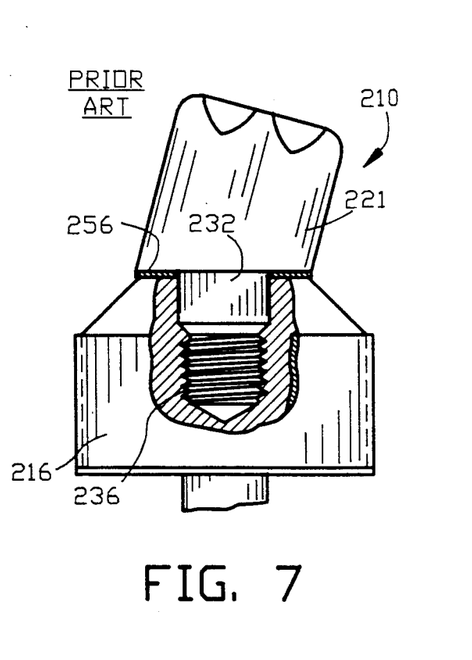
FIG. 7 is a side view partially in section of the third prior art dental implant.

FIGS. 6 and 7 illustrate a third prior art dental implant 210 as disclosed in U.S. Pat. No. 4,531,915 to mount a support 221 in a proper rotational position relative to the boss 216. The support 221 includes a stud 232 having a shank portion 234 and a threaded portion 236 which extends angularly from the support 221. The rotational position of the angular position of the support 221 may be varied by incorporating a washer 256 between the support 221 and the boss 216 with the thickness of the washer 256 being in proportion to the slope of the threads of the threaded portion 236 to determine the rotational position of the support 221.

Although these two devices proposed in U.S. Pat. No. 4,531,915 for rotatably mounting an angularly disposed support relative to the boss has provided a significant advancement in the art, it is the purpose of the present invention to improve upon the devices proposed in U.S. Pat. No. 4,531,915.

FIGS. 8-11 illustrate a first embodiment of a dental implant post 310 incorporating the present invention. The dental implant post 310 comprises a boss 316 secured to an implant anchor such as a rod 312 and fins as illustrated in FIGS. 1-4 for securing the boss 316 relative to the jawbone of a patient. It should be appreciated by those skilled in the art that the present invention may be incorporated into virtually any type of dental implant and should not be limited to any specific type or design of implant anchor.

Figure 8:
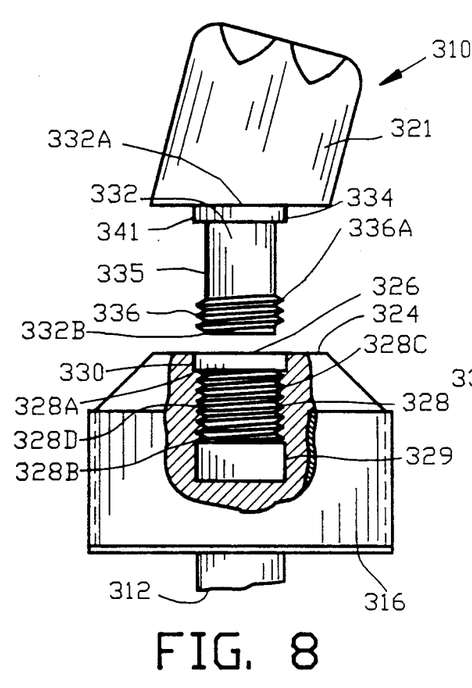
FIG. 8 is an exploded side view partially in section of a first embodiment of dental implant post incorporating the present invention.

A counterbore 326 is axially disposed within the upper surface 324 of boss 316 with a threaded hole 328 extending concentrically from the bottom of the counterbore 326 into the boss 316 between an outer end 328A and an inner end 328B. The diameter of counterbore 326 is greater than the diameter of the threaded hole 328 defining a boss shoulder 330 at the junction of the counterbore 326 and the threaded hole 328. An undercut 329 is defined at the inner end 328B of the threaded hole 328. The undercut 329 has a diameter which is slightly larger than an outside thread diameter 328C of the threaded hole 328 and is significantly larger than an inside thread diameter 328D of the threaded hole 328.

A stud 332 extends angularly from the support 321 between a proximal end 332A and a distal end 332B. The stud 332 has a shank portion 334, an intermediate portion 335 and a threaded portion 336. The diameter of the shank portion 334 is greater than the diameter of the intermediate portion 335 defining a stud shoulder 341 at the junction of the shank portion 334 and the intermediate portion 335. An outside thread diameter 336A of the threaded portion 336 is greater than the diameter of the intermediate portion 335.

The diameter and the axial length of the counterbore 326 of the boss 316 is commensurate with the diameter and axial length of the shank portion 334 of the stud 332 for providing a rotational fit between the stud 332 and the boss 316. The axial length of the threaded hole 328 of the boss 316 is slightly less than the axial length of the intermediate portion 335 of the stud 332. The diameter and the axial length of the undercut 329 of the boss 316 is slightly greater than the axial length and the outside thread diameter 336A of the threaded portion 336 of the stud 332 for providing a rotational fit between the stud 332 and the boss 316.

Figure 9:
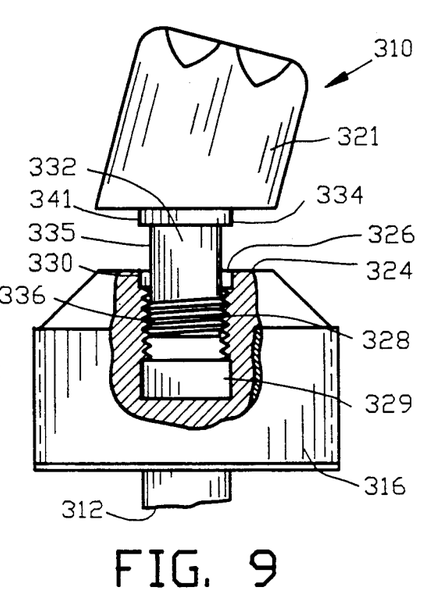
FIG. 9 is a side view partially in section of the dental implant post of FIG. 8 illustrating the threading of a shank into a boss.

FIG. 9 is a side view partially in section of the dental implant post 310 of FIG. 8 illustrating the threading of the threaded portion 336 of the stud 332 into the threaded hole 328 of the boss 316. Preferably the threaded hole 328 of the boss 312 and the threaded portion 336 of the stud 332 comprise lefthanded threads which will not loosen but rather tighten when subjected to any grinding procedures by a dentist.

Figure 10:
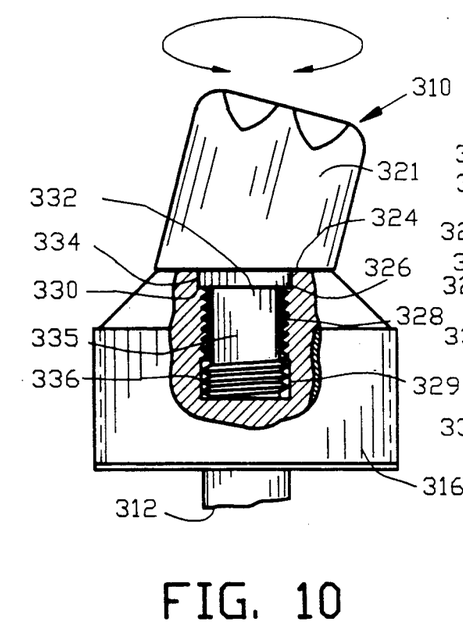
FIG. 10 is a side view partially in section of the dental implant post of FIG. 8 illustrating the completion of the threading of the shank into the boss.

FIG. 10 is a side view partially in section of the dental implant post 310 of FIG. 8 illustrating the completion of insertion of the stud 332 into the boss 316. Since the axial length of the shank portion 334 of the stud 332 is equal to the axial length of the counterbore 326 of the boss 316, the stud shoulder 341 engages with the boss shoulder 330 when the shank portion 334 is received with the counterbore 326 to provide an upper rotational fit between the shank portion 334 of the stud 332 and the counterbore 326 of the boss 316. Concomitantly therewith, the threaded portion 336 of the stud 332 is received within the undercut 329 of the boss 316 to provide a lower rotational fit between the stud 332 and the boss 316.

Figure 11:
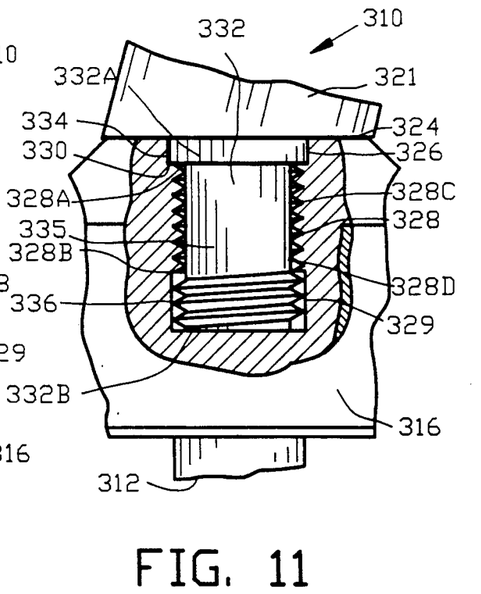
FIG. 11 is an enlarged partial view of FIG. 10.

FIG. 11 is an enlarged partial view of FIG. 10 further illustrating the threaded portion 336 of the stud 332 being positioned within the undercut 329 of the boss 316. The stud 332 can rotated about the axis of the threaded hole 328 without linear movement along the axis of the threaded hole 328. The threaded portion 336 of the stud 332 within the undercut 329 of the boss 316 maintains the axial position of the stud 332 relative to the boss 316 during rotational movement of the stud 332 relative to the boss 316. However, the stud 332 may be removed from the boss 316 by applying an extracting or outward force to the stud 332 and unthreading the stud 332 from the boss 316.

The dental implant post 310 of FIGS. 8-11 is inserted within a socket of a recently extracted tooth or an artificially created socket in a manner to the prior art implants of FIGS. 1-7. A conventional cap screw (not shown) is threaded into the threaded hole 328 of boss 316. After the dental implant remains in place for a period of time to rigidly secure the dental implant post 310 within the socket, the conventional cap screw is removed and the support 321 is threaded into the boss 316. After preliminary rotational alignments or adjustments are made to the support 321 and/or the prosthesis 11, then a cement is applied to the stud 332 and/or the boss 316 and the stud 332 is threaded and rigidly secured to the boss 316. The prosthesis 11 is supported by support 321 through the upper rotational fit between the shank portion 334 and the counterbore 326 a lower rotational fit between the threaded portion 336 and the undercut 329.

FIGS. 12-15 illustrate a second embodiment of a dental implant post 410 incorporating the present invention. The dental implant post 410 comprises a boss 416 secured to an implant anchor such as a rod 412 and fins (not shown) for securing the boss 416 relative to the jawbone of a patient.

Figure 12:
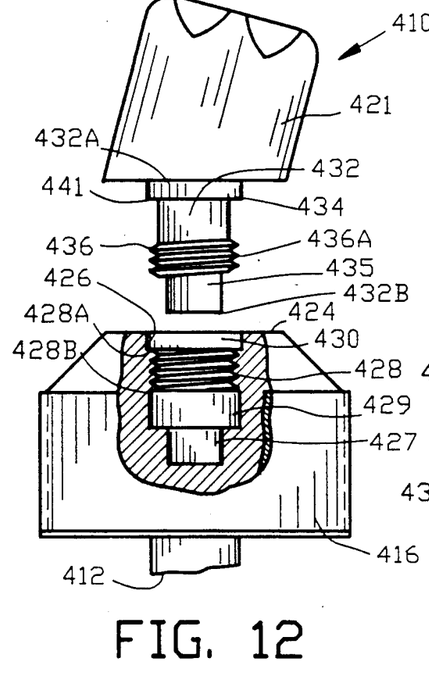
FIG. 12 is an exploded side view partially in section of a second embodiment of the dental implant post incorporating the present invention.

A counterbore 426 is axially disposed within the upper surface 424 of boss 416 with a threaded hole 428 extending concentrically from the bottom of the counterbore 426 into the boss 416 between an outer end 428A and an inner end 428B. A receiver bore 427 extends concentrically from the inner end 428A of the threaded hole 428. The diameter of counterbore 426 is greater than the diameter of the threaded hole 428 defining a boss shoulder 430 at the junction of the counterbore 426 and the threaded hole 428. An undercut 429 is defined between the outer end 428A and inner end 428B of the threaded hole 428. The undercut 429 has a diameter which is slightly larger than an outside thread diameter 428C of the threaded hole 428 and is significantly larger than an inside thread diameter 428D of the threaded hole 428. The receiver bore 427 has a diameter which is smaller than the inside thread diameter 428D of the threaded hole 428.

A stud 432 extends angularly from the support 421 between a proximal end 432A and a distal end 432B. Typically the stud 432 extends at an angle of ten (10) to sixty (60) degrees from the support 421. The stud 432 has a shank portion 434, an distal portion 435 and a threaded portion 436. The diameter of the shank portion 434 is greater than the diameter of the distal portion 435 defining a stud shoulder 441 at the junction of the shank portion 434 and the distal portion 435. An outside thread diameter 436A of the threaded portion 436 is greater than the diameter of the distal portion 435.

The diameter and the axial length of the counterbore 426 of the boss 416 is commensurate with the diameter and axial length of the shank portion 434 of the stud 432 for providing an upper rotational fit between the stud 432 and the boss 416. The diameter and the axial length of the receiver bore 427 of the boss 416 is commensurate with the diameter and axial length of the distal portion 435 of the stud 432 for providing a lower rotational fit between the stud 432 and the boss 416. The distance between the undercut 429 and the boss shoulder 430 is equal to the distance between the threaded portion 336 and the stud shoulder 441. The diameter and the axial length of the undercut 429 of the boss 416 is slightly greater than the axial length and the outside thread diameter 436A of the threaded portion 436 of the stud 432 for providing an intermediate rotational fit between the stud 432 and the boss 416.

Figure 13:
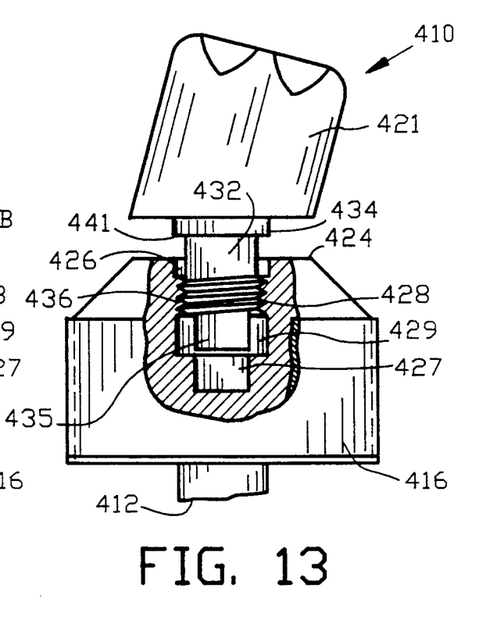
FIG. 13 is a side view partially in section of the dental implant post of FIG. 12 illustrating the threading of a shank into a boss.
Figure 14:
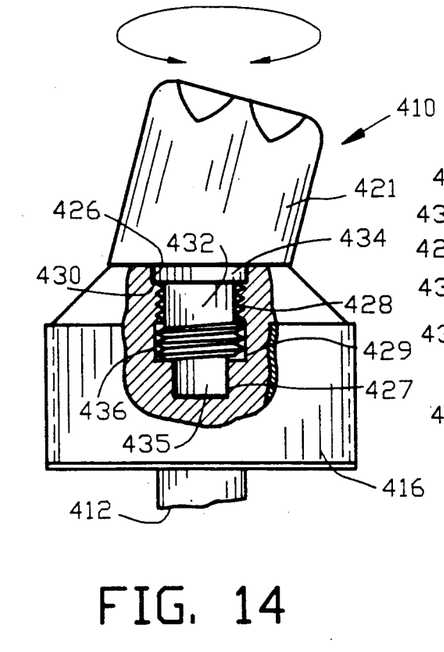
FIG. 14 is a side view partially in section of the dental implant post of FIG. 12 illustrating the completion of the threading of the shank into the boss.

FIG. 13 is a side view partially in section of the dental implant post 410 of FIG. 12 illustrating the threading of the threaded portion 436 of the stud 432 into the threaded hole 428 of the boss 416 whereas FIG. 14 illustrates the completion of insertion of the stud 432 into the boss 416. Since the axial length of the shank portion 434 of the stud 432 is equal to the axial length of the counterbore 426 of the boss 416, the stud shoulder 441 engages with the boss shoulder 430 when the shank portion 434 is received with the counterbore 426 to provide an upper rotational fit between the shank portion 434 of the stud 32 and the counterbore 426 of the boss 416. The threaded portion 436 of the stud 432 is received within the undercut 429 of the boss 416 to provide an intermediate rotational fit between the stud 432 and the boss 416. In addition, distal portion 435 of the stud 432 is received within the receiver bore 427 of the boss 416 to provide a lower rotational fit between the stud 432 and the boss 416.

Figure 15:
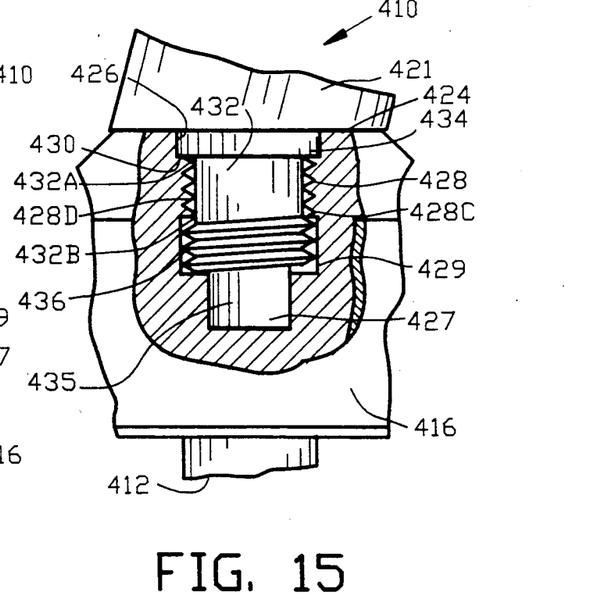
FIG. 15 is an enlarged partial view of FIG. 14.

FIG. 15 is an enlarged partial view of FIG. 10 further illustrating the threaded portion 436 of the stud 432 being positioned within the undercut 429 of the boss 416. In a manner similar to FIGS. 8-11, the stud 432 can be rotated about the axis of the threaded hole 428 without linear movement along the axis of the threaded hole 428. The threaded portion 436 of the stud 432 within the undercut 429 of the boss 416 maintains the axial position of the stud 432 relative to the boss 416 during rotational movement of the stud 43 relative to the boss but may be removed by applying an extracting or outward force to the stud 432 and unthreading the stud 432 from the boss 416

After preliminary rotational alignments or adjustments are made to the support 421 and/or the prosthesis 11, a cement is applied to the stud 432 and/or the boss 416 and the stud 432 is threaded and rigidly secured to the boss 416. The prosthesis 11 is supported by support 421 through the upper rotational fit between the shank portion 434 and the counterbore 426, the intermediate rotational fit between the threaded portion 436 of the stud 432 and the a lower rotational fit between the distal portion 435 and the receiver bore 427.

FIGS. 16-21 illustrate a third embodiment of a dental implant post 510 incorporating the present invention. The dental implant post 510 comprises a boss 516 secured to an implant anchor such as a rod 512 and fins (not shown) for securing the boss 516 relative to the jawbone of a patient.

Figure 16:
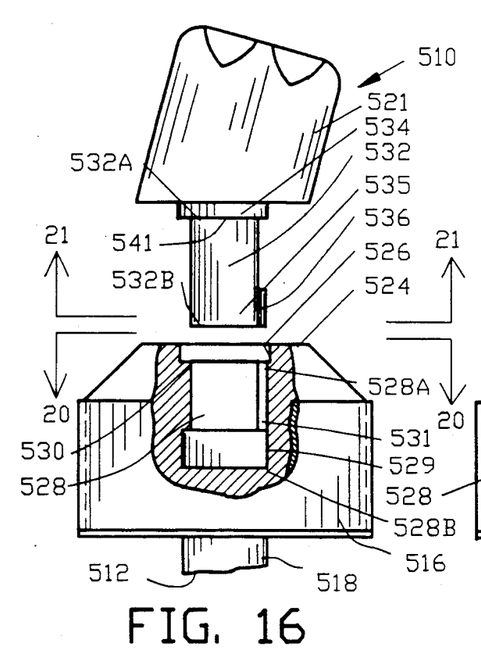
FIG. 16 is an exploded side view partially in section of a third embodiment of the dental implant post incorporating the present invention.

A counterbore 526 is axially disposed within the upper surface 524 of boss 516 with a boss hole 528 extending concentrically from the bottom of the counterbore 526 into the boss 516 between an outer end 528A and an inner end 528B. The diameter of counterbore 526 is greater than the diameter of the boss hole 528 defining a boss shoulder 530 at the junction of the counterbore 526 and the boss hole 528. An undercut 529 at the inner end 528B of the boss hole 528. A keyway 531 extends outwardly from the boss hole 528 along the length of the boss hole 528 between the outer end 528A and an inner end 528B. The undercut 529 has a diameter which is substantially equal to the outside diameter of the keyway 531 and is significantly larger than an inside diameter 528D of the boss hole 528.

A stud 532 extends angularly from the support 521 between a proximal end 532A and a distal end 532B. The stud 532 has a shank portion 534, an distal portion 535. A key 536 extends outwardly from the distal portion 535 of the stud 532. The diameter of the shank portion 534 is greater than the diameter of the distal portion 535 defining a stud shoulder 541 at the junction of the shank portion 534 and the distal portion 535.

The diameter and the axial length of the counterbore 526 of the boss 516 is commensurate with the diameter and axial length of the shank portion 534 of the stud 532 for providing an upper rotational fit between the stud 532 and the boss 516. The distance between the undercut 529 and the boss shoulder 530 is equal to the distance between the key 536 and the stud shoulder 541. The diameter and the axial length of the undercut 529 of the boss 516 is slightly greater than the axial length and the outside diameter 536A of the key 536 of the stud 532 for providing an intermediate rotational fit between the stud 532 and the boss 516.

Figure 17:
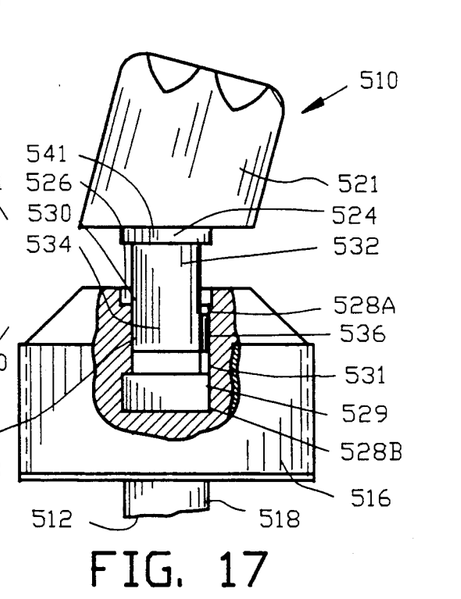
FIG. 17 is a side view partially in section of the dental implant post of FIG. 16 illustrating the partial insertion of a keyed shank into a kewyay in a boss.
Figure 18:
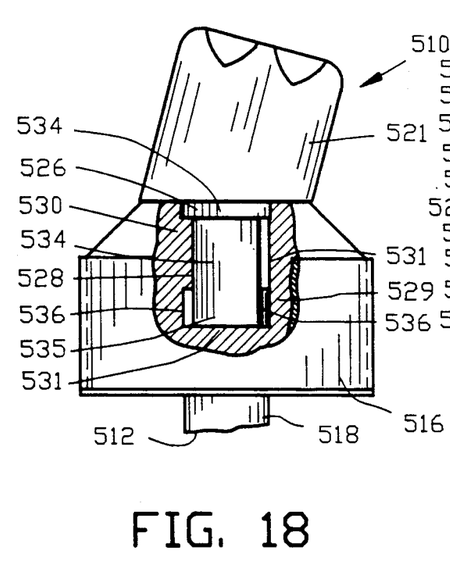
FIG. 18 is a side view partially in section of the dental implant post of FIG. 16 illustrating the completion of the insertion of the shank into the boss.
Figure 19:
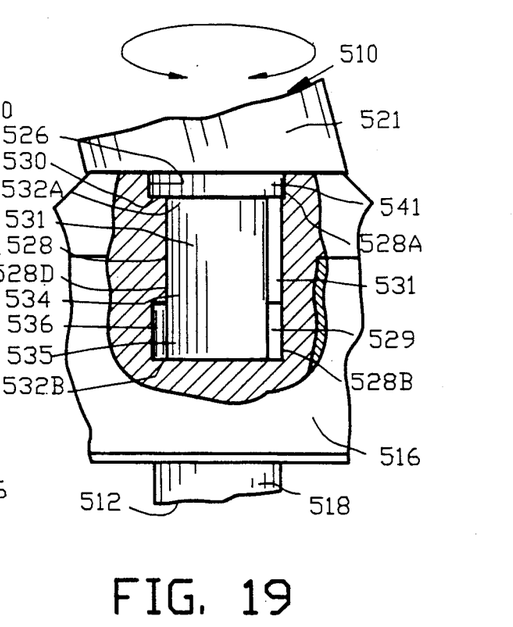
FIG. 19 is an enlarged partial view of FIG. 18 with the shank rotated.
Figure 20:
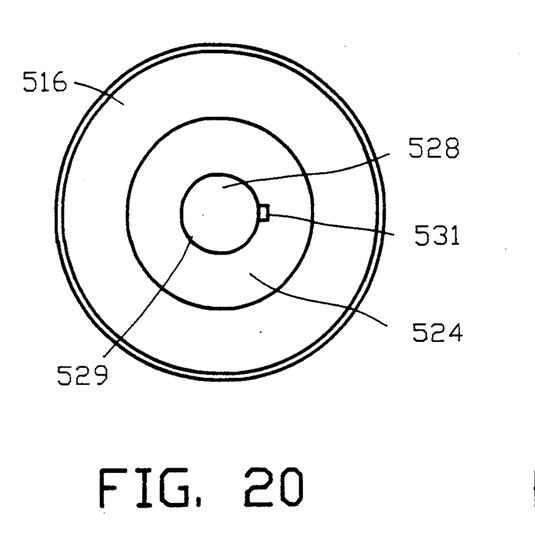
FIG. 20 is a view along line 20—20 in FIG. 16.
Figure 21:
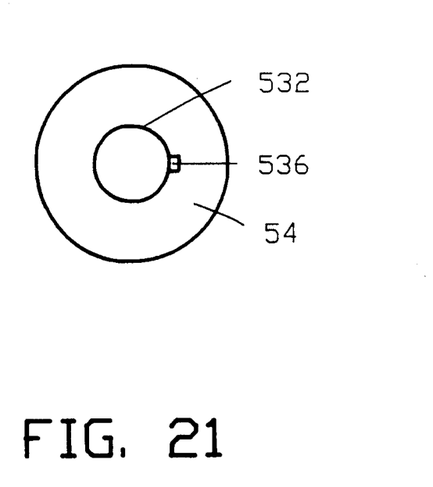
FIG. 21 is a view along line 21—21 in FIG. 16.

FIG. 17 is a side view partially in section of the dental implant post 510 of FIG. 16 illustrating the insertion of the key 536 of the stud 532 into the keyway 531 of boss hole 528 of the boss 516 whereas FIG. 18 illustrates the completion of insertion of the stud 532 into the boss 516. Since the axial length of the shank portion 534 of the stud 532 is equal to the axial length of the counterbore 526 of the boss 516, the stud shoulder 541 engages with the boss shoulder 530 when the shank portion 534 is received with the counterbore 526 to provide an upper rotational fit between the shank portion 534 of the stud 532 and the counterbore 526 of the boss 516. The key 536 of the stud 532 is received within the undercut 529 of the boss 516 to provide a rotational fit between the stud 532 and the boss 516.

FIG. 18 is an enlarged partial view of FIG. 10 further illustrating the rotation of the stud 532 within the undercut 529 of the boss 516. In a manner similar to FIGS. 8-11, the stud 532 can be rotated about the axis of the boss hole 528 without linear movement along the axis of the boss hole 528. The key 536 of the stud 532 within the undercut 529 of the boss 516 maintains the axial position of the stud 532 relative to the boss 516 during rotational movement of the stud 532 relative to the boss 516 but may be removed by aligning the key 536 with the keyway 531 and applying an extracting or outward force to the stud 532.

After preliminary rotational alignments or adjustments are made to the support 521 and/or the prosthesis 11, a cement is applied to the stud 532 and/or the boss 516 and the stud 532 is inserted and rigidly secured to the boss 516. The prosthesis 11 is supported by support 521.

Figures 22, 23:
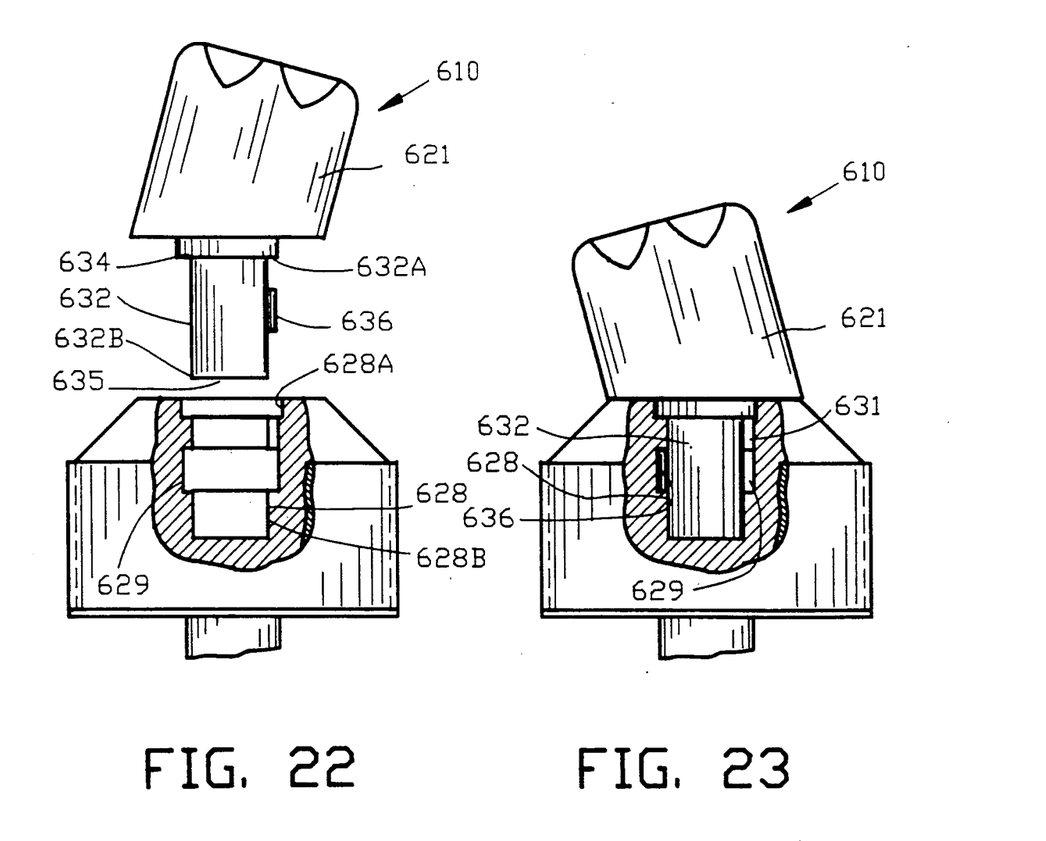
FIG. 22 is an exploded side view partially in section of a fourth embodiment of the dental implant post incorporating the present invention.
FIG. 23 is a side view partially in section of the dental implant post of FIG. 22 illustrating the complete insertion and rotation of the shank within the boss.

FIGS. 22 and 23 illustrate a fourth embodiment of a dental implant post 610 incorporating the present invention. The dental implant post 610 is similar to the dental implant post of FIGS. 16-21 with a keyway 631 extends outwardly from the boss hole 628 along a partial length of the boss hole 628 between an outer end 628A and an inner end 628B. The undercut 629 has a diameter which is substantially equal to the outside diameter of the keyway 631 is positioned intermediate the outer end 628A and the inner end 628B boss hole 628.

A stud 632 extends angularly from the support 621 between a proximal end 632A and a distal end 632B. A key 636 extends outwardly from the distal portion 635 of the stud 632 on the stud 632, to be in alignment with the undercut 629 when the stud 632 is inserted into the boss hole 628 as shown in FIG. 23.

The present invention discloses an improved means for rotationally orientating the prosthesis support relative to an implant anchor. The rotary dental implant post provides a simple, strong and efficient apparatus for allowing a support to be rotationally positioned prior to the final mounting of the prosthesis.

The present disclosure includes that contained in the appended claims as well as that of the foregoing description. Although this invention has been described in its preferred form with a certain degree of particularity, it is understood that the present disclosure of the preferred form has been made only by way of example and that numerous changes in the details of construction and the combination and arrangement of parts may be resorted to without departing from the spirit and scope of the invention.

What is claimed is:

1. A dental implant post for supporting a prosthesis in a patient, comprising:
   a boss having a boss hole defining a boss hole recess;
   an implant anchor for securing said boss relative to the patient;
   a support for supporting the prosthesis;
   a stud having stud projection means secured relative to said support; and
   an undercut defined in said boss enabling said stud projection means to be moved along said bore hole recess and to enter said undercut for enabling free rotation of said support relative to said boss and for inhibiting vertical movement of said stud relative to said boss.

2. A dental implant post for supporting a prosthesis as set forth in claim 1, including a counterbore defined in said boss and disposed concentrically with said boss hole; and
   said stud having a shank portion for providing a rotational fit with said counterbore defined in said boss when said stud projection means is disposed within said undercut.

3. A dental implant post for supporting a prosthesis as set forth in claim 2, wherein said counterbore has a diameter which is greater than a diameter of said boss hole for defining a boss shoulder at a junction of said counterbore and said boss hole;
   said stud including a shank portion, an intermediate portion with said shank portion having a diameter which is greater than a diameter of said intermediate portion for defining a stud shoulder at a junction of said shank portion and said intermediate portion; and
   said shank portion providing a rotational fit with said counterbore when said stud threads are disposed within said undercut.

4. A dental implant post for supporting a prosthesis as set forth in claim 1, wherein said stud projection means has an axial length which is commensurate to an axial length of said undercut.

5. A dental implant post for supporting a prosthesis as set forth in claim 1, wherein said stud extends angularly from a bottom surface of said support.

6. A dental implant post for supporting a prosthesis as set forth in claim 1, wherein said undercut is defined in said boss at an inner end of said bore hole;
   said stud having a proximal end and a distal end with said proximal end being secured to said support; and
   said stud projection means being disposed at said distal end of said stud.

7. A dental implant post for supporting a prosthesis as set forth in claim 1, wherein said undercut has a diameter which is commensurate in diameter with an outside diameter of said stud projection means.

8. A dental implant post for supporting a prosthesis as set forth in claim 1, including means for inhibiting rotation of said support relative to said boss.

9. A dental implant post for supporting a prosthesis as set forth in claim 1, including cement means for inhibiting rotation of said support relative to said boss.

10. A dental implant post for supporting a prosthesis as set forth in claim 1, wherein said boss hole recess includes boss threads defined in said boss hole; and
said stud projection means comprising stud threads secured relative to said support for mating engaging with said boss threads.

11. A dental implant post for supporting a prosthesis as set forth in claim 1, wherein said boss hole recess includes boss keyway defined in said boss hole; and
said stud projection means comprising a key extending outwardly from said support for mating engaging with said keyway.

12. A dental implant post for supporting a prosthesis in a patient, comprising:
a boss having a threaded hole defining boss threads;
an implant anchor for securing said boss relative to the jawbone of the patient;
a support for supporting the prosthesis;
a stud having stud threads secured relative to said support; and
an undercut defined in said boss enabling said stud threads to be threaded into said boss threads and to enter said undercut for enabling free rotation of said support relative to said boss.

13. A dental implant post for supporting a prosthesis as set forth in claim 12, including a counterbore defined in said boss and disposed concentrically with said threaded hole; and
said stud having a shank portion for providing a rotational fit with said counterbore defined in said boss when said stud threads are disposed within said undercut.

14. A dental implant post for supporting a prosthesis as set forth in claim 13, wherein said counterbore has a diameter which is greater than a diameter of said threaded hole for defining a boss shoulder at a junction of said counterbore and said threaded hole;
said stud including a shank portion, an intermediate portion and a threaded portion with said shank portion having a diameter which is greater than a diameter of said intermediate portion for defining a stud shoulder at a junction of said shank portion and said intermediate portion; and
said shank portion providing a rotational fit with said counterbore when said stud threads are disposed within said undercut.

15. A dental implant post for supporting a prosthesis as set forth in claim 12, wherein said stud threads have an axial length which is commensurate to an axial length of said undercut.

16. A dental implant post for supporting a prosthesis as set forth in claim 12, wherein said stud extends angularly from a bottom surface of said support.

17. A dental implant post for supporting a prosthesis as set forth in claim 12, wherein said undercut is defined in said boss at an inner end of said threaded hole;
said stud having a proximal end and a distal end with said proximal end being secured to said support; and
said stud threads being disposed only at said distal end of said stud.

18. A dental implant post for supporting a prosthesis as set forth in claim 12, wherein said undercut has a diameter which is commensurate in diameter with an outside thread diameter of said stud threads.

19. A dental implant post for supporting a prosthesis as set forth in claim 12 including means for inhibiting rotation of said support relative to said boss.

20. A dental implant post for supporting a prosthesis as set forth in claim 12, including cement means for inhibiting rotation of said support relative to said boss.

21. A dental implant post for supporting a prosthesis relative to a jawbone of a patient, comprising:
a boss having a threaded hole defining boss threads;
fin means connected to said boss for securing said boss relative to the jawbone of the patient;
a support for supporting the prosthesis;
a stud having stud threads secured relative to said support; and
an undercut defined in said boss enabling said stud threads to be threaded into said boss threads and to enter said undercut for enabling free rotation of said support relative to said boss.

22. A dental implant post for supporting a prosthesis as set forth in claim 21, including a counterbore defined in said boss and disposed concentrically with said threaded hole; and
said stud having a shank portion for providing a rotational fit with said counterbore defined in said boss when said stud threads are disposed within said undercut.

23. A dental implant post for supporting a prosthesis as set forth in claim 22, wherein said counterbore has a diameter which is greater than a diameter of said threaded hole for defining a boss shoulder at a junction of said counterbore and said threaded hole;
said stud including a shank portion, an intermediate portion and a threaded portion with said shank portion having a diameter which is greater than a diameter of said intermediate portion for defining a stud shoulder at a junction of said shank portion and said intermediate portion; and
said shank portion providing a rotational fit with said counterbore when said stud threads are disposed within said undercut.

24. A dental implant post for supporting a prosthesis as set forth in claim 21, wherein said stud threads have an axial length which is commensurate to an axial length of said undercut.

25. A dental implant post for supporting a prosthesis as set forth in claim 21, wherein said stud extends angularly from a bottom surface of said support.

26. A dental implant post for supporting a prosthesis as set forth in claim 21, wherein said undercut is defined in said boss at an inner end of said threaded hole;
said stud having a proximal end and a distal end with said proximal end being secured to said support; and
said stud threads being disposed only at said distal end of said stud.

27. A dental implant post for supporting a prosthesis as set forth in claim 21, wherein said undercut has a diameter which is commensurate in diameter with an outside thread diameter of said stud threads.

28. A dental implant post for supporting a prosthesis as set forth in claim 21, including means for inhibiting rotation of said support relative to said boss.

29. A dental implant post for supporting a prosthesis as set forth in claim 21, including cement means for inhibiting rotation of said support relative to said boss.

30. A dental implant post for supporting a prosthesis relative to a jawbone of a patient, comprising:
a boss having a threaded hole defining boss threads;
an implant anchor for securing said boss relative to the jawbone of the patient;
a counterbore defined in said boss and disposed concentrically with said threaded hole;
a support for supporting the prosthesis;
a stud extending angularly from said support between a proximal end and a distal end;
said stud having a shank disposed at said proximal end of said stud and having stud threads being disposed only at said distal end of said stud; and
an undercut defined in said boss enabling said stud threads to be threaded into said boss threads and to enter said undercut for enabling free rotation of said support relative to said boss with said shank portion providing a rotational fit with said counterbore.

31. A dental implant post for supporting a prosthesis as set forth in claim 30, including cement means for inhibiting rotation of said support relative to said boss.

* * * * *